(12) United States Patent
Olson et al.

(10) Patent No.: US 6,613,061 B1
(45) Date of Patent: Sep. 2, 2003

(54) DEVICE FOR TRANSPLANTING A CORNEA ON A PATIENT'S EYE

(76) Inventors: Randall J. Olson, 50 N. Medical Dr., Salt Lake City, UT (US) 84132; Rolf Meyer, Bellvueweg 22, CH-2562 Biel (CH)

( * ) Notice: Subject to any disclaimer, the term of this patent is extended or adjusted under 35 U.S.C. 154(b) by 121 days.

(21) Appl. No.: 09/658,869

(22) Filed: Sep. 8, 2000

(51) Int. Cl.[7] .................................................. A61F 9/00
(52) U.S. Cl. ...................................................... 606/166
(58) Field of Search ................................ 606/166, 167, 606/170, 180, 181, 161, 179; 30/130, 301, 316

(56) References Cited

U.S. PATENT DOCUMENTS

| | | | |
|---|---|---|---|
| 2,838,050 A | | 6/1958 | Ara |
| 3,074,407 A | * | 1/1963 | Moon et al. ................. 606/166 |
| 4,423,728 A | | 1/1984 | Lieberman |
| 4,429,696 A | * | 2/1984 | Hanna et al. ................ 606/166 |
| 4,997,437 A | * | 3/1991 | Grieshaber ................... 606/166 |
| 5,011,498 A | * | 4/1991 | Krumeich et al. .......... 606/166 |
| 5,063,942 A | * | 11/1991 | Kilmer et al. ............... 128/898 |
| 5,258,002 A | | 11/1993 | Jeffers et al. |
| 5,336,236 A | | 8/1994 | Nevyas-Wallace |
| 5,391,177 A | | 2/1995 | Schwartz |
| 5,423,330 A | | 6/1995 | Lee |

FOREIGN PATENT DOCUMENTS

| | | |
|---|---|---|
| DE | 37 07 004 A1 | 9/1988 |
| DE | 198 03 175 A1 | 7/1999 |
| EP | 0 047 190 A2 | 3/1982 |
| EP | 0 251 485 A1 | 5/1987 |
| FR | 1366323 A | 11/1964 |
| GB | 2113550 | * 8/1983 |
| GB | 2242835 | * 10/1991 |
| RU | 2 010 558 C1 | 4/1994 |

* cited by examiner

*Primary Examiner*—Michael J. Milano
*Assistant Examiner*—Vy Q. Bui
(74) *Attorney, Agent, or Firm*—Browdy and Neimark, P.L.L.C.

(57) ABSTRACT

The device comprises a tubular housing having an axis and comprising a suction ring on its lower end face with an annular recess communicating with a corretor for connection to a suction pump. The housing has first stop means and second stop means. A tubular insert is mounted in the housing for rotation around the axis and axially displacable. The insert has a third stop means cooperating with the first stop means for defining an extended position of the insert and a fourth stop means coacting with the second stop means for defining a retracted position of the insert. The insert further has a micrometer female thread. A tubular knife holder with a knife for cutting a circular cut into the cornea is mounted in the insert. The knife holder has a micrometer male thread threaded into the female thread and a head. A scale and a marking on the head and on the insert are provided for preselecting a depth of the cut in the extended position of the insert.

8 Claims, 3 Drawing Sheets

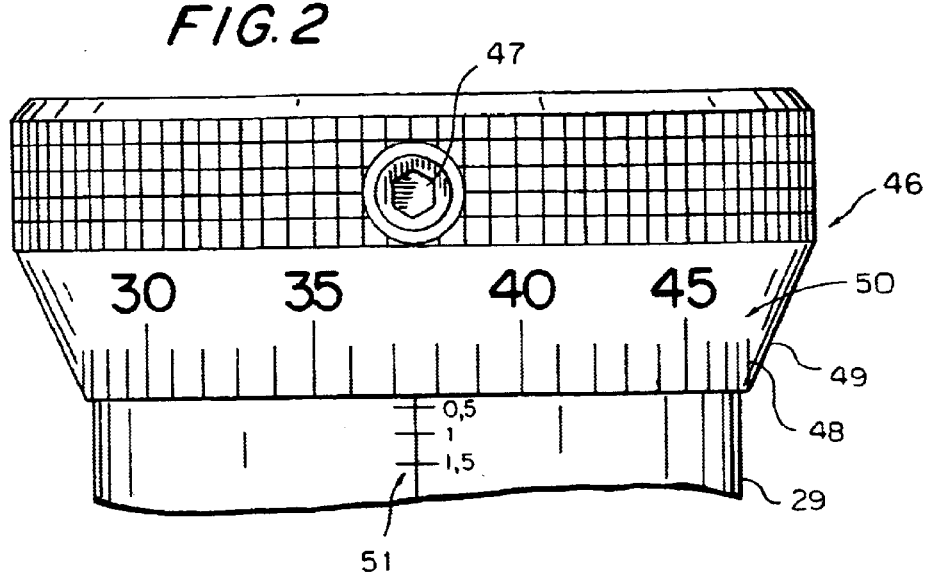
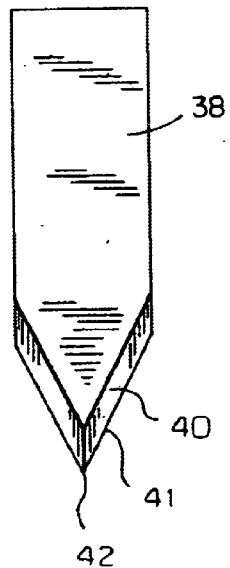
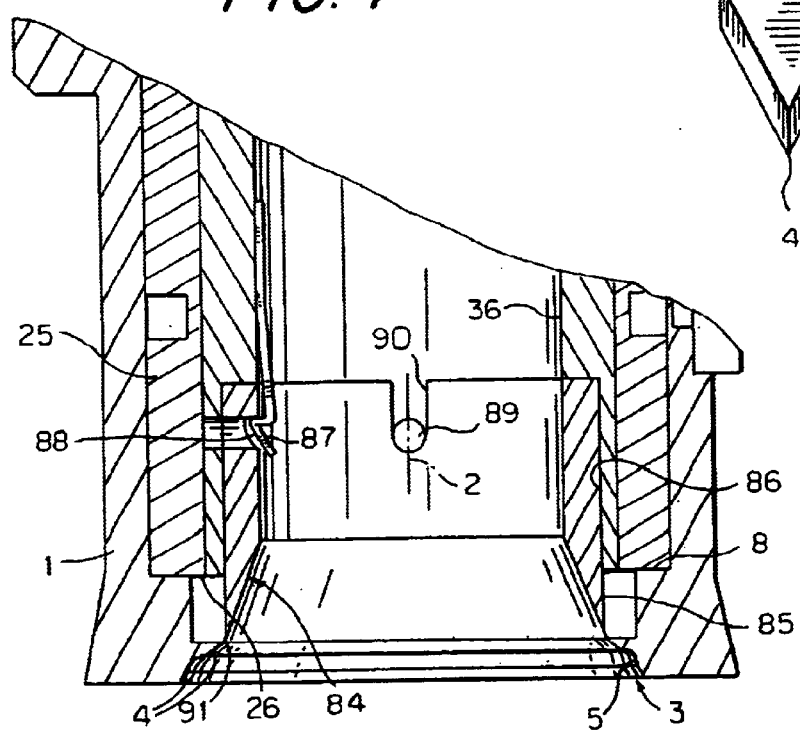

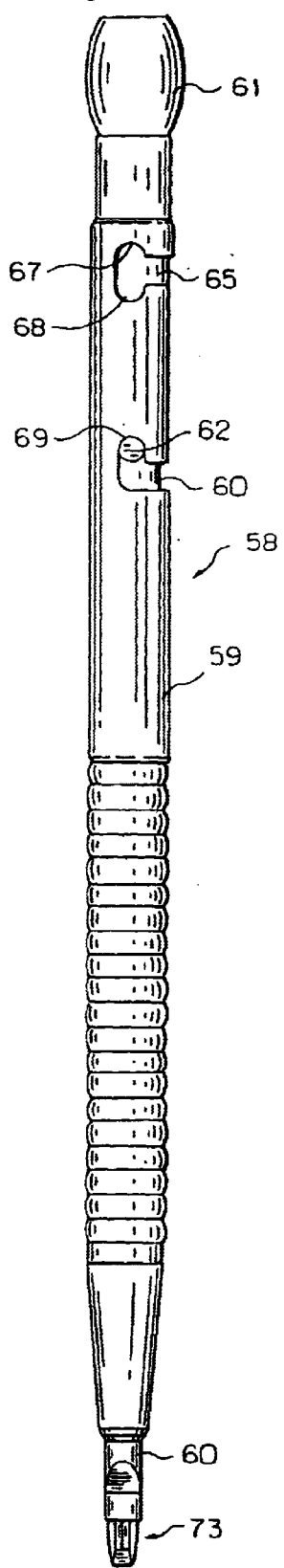
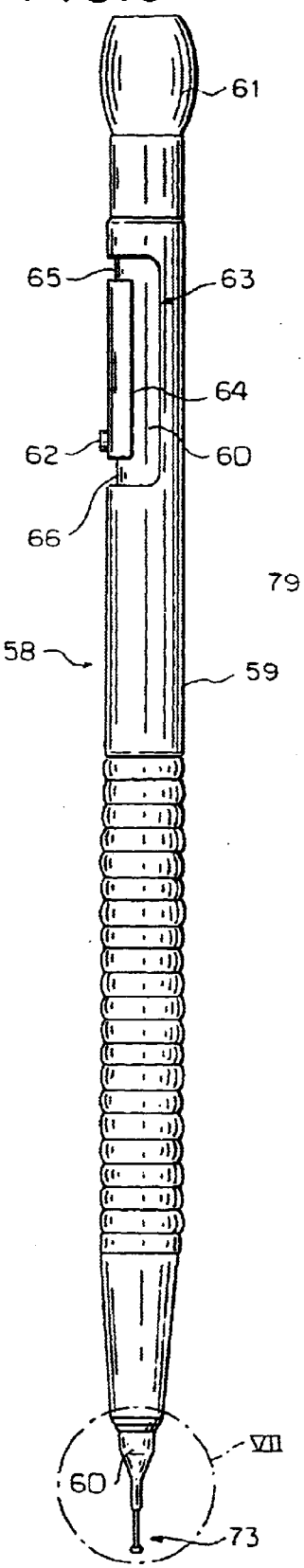
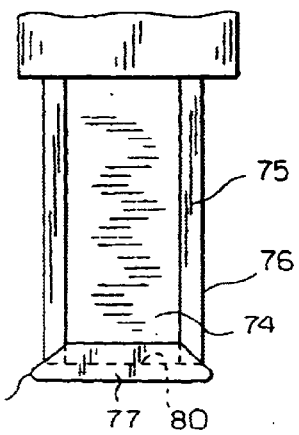
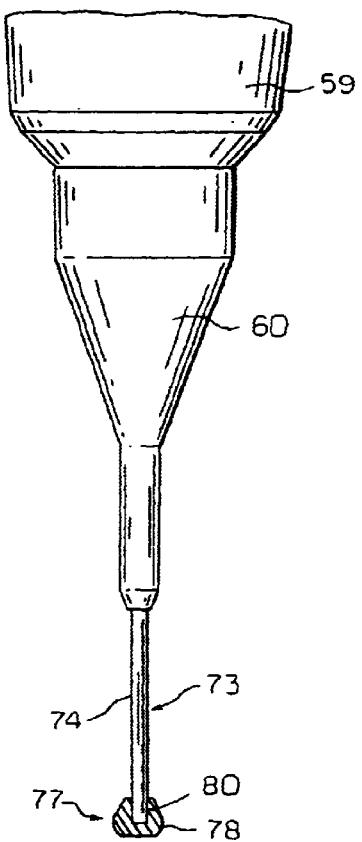

DEVICE FOR TRANSPLANTING A CORNEA ON A PATIENT'S EYE

FIELD AND BACKGROUND OF THE INVENTION

For transplanting cornea onto a patient's eye a circular transplant is prepared. The cornea of the patient's eye is marked with a circle and cut along that circle with special scissors. The cut out circular piece is removed. The transplant is then inserted and sown to the remaining cornea.

SUMMARY OF THE INVENTION

It is an object of the present invention to increase the safety and accuracy of the transplanting operation and to reduce its length. This object and others which will become apparent as the description progresses is achieved by the present invention, which, briefly stated, concerns a device for transplanting a cornea on a patient's eye. The device comprises a tubular housing having an axis and comprising a suction ring on its lower end face with an annular recess communicating with a connector for connection to a suction pump. The housing has first stop means and second stop means. A tubular insert is mounted in the housing for rotation around the axis and axially displaceable. The insert has a third stop means cooperating with the first stop means for defining an extended position of the insert and a fourth stop means coacting with the second stop means for defining a retracted position of the insert. The insert further has a micrometer female thread. A tubular knife holder with a knife for cutting a circular cut into the cornea is mounted in the insert. The knife holder has a micrometer male thread threaded into the female thread and a head. A scale and a marking on the head and on the insert are provided for preselecting a depth of the cut in the extended position of the insert.

BRIEF DESCRIPTION OF THE DRAWINGS

Preferred embodiments of the present invention are hereinafter described with reference to the drawings, in which FIG. 2 shows a side view of the upper end, FIG. 3 shows a side view of the diamond knife FIG. 4 shows an axial section through a lower end of a second embodiment, FIGS. 5 and 6 show side views of a scalpel, and FIGS. 7 and 8 show side views of details of the knife of the scalpel.

DETAILED DESCRIPTION OF THE PREFERRED EMBODIMENT(S) OF THE INVENTION

Figure 1:
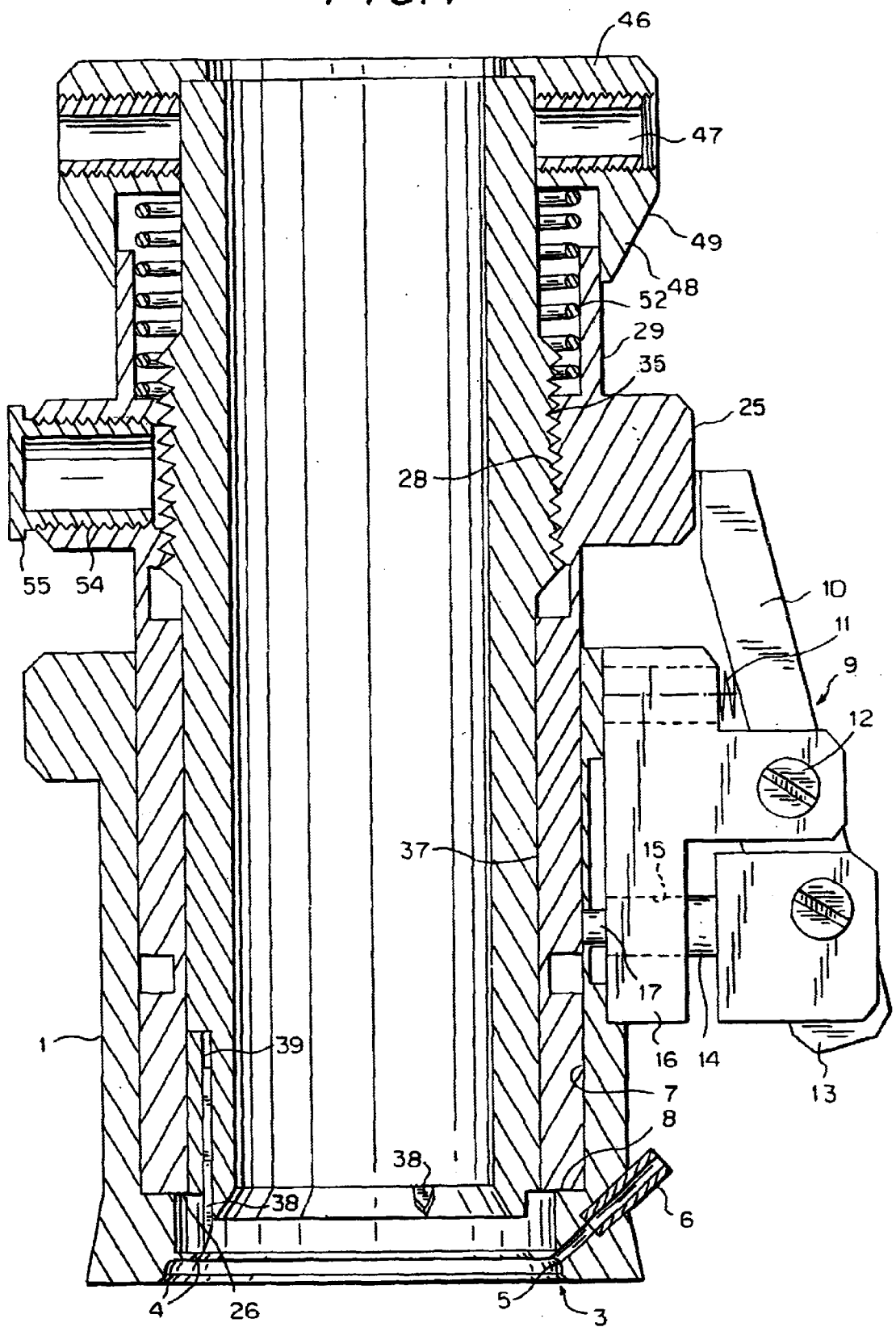
FIG. 1 shows an axial section through a first embodiment.

The device according to FIGS. 1–3 comprises a tubular housing 1 having an axis 2. At its lower end face the housing 1 has a suction ring 3 with two concentric spherical contact surfaces 4 of equal radius separated by an annular recess 5. The recess 5 communicates with a connector 6 for connection with a suction pump. The housing 1 has a cylindrical boring 7 which ends at a plane radial shoulder 8 forming a stop. A second stop means 9 is mounted on one side of the housing. It comprises a lever 10 preloaded by a spring 11 and pivotable around an axis 12. On the lower lever arm 13 a pin 14 is pivotably attached. The pin 14 is guided in a transverse boring 15 of a holder 16 screwed to the housing 1. The cylindrical front end 17 of the pin 14 serves as a stop for the retracted position of a tubular insert 25 which is guided in the boring 7 for rotation around the axis 2 and for axial movement along that axis.

The insert 25 is shown in the extended position in which its planar front end face 26 constituting a third stop means abuts the shoulder 8. In the retracted position of the insert 25 the end 17 of the pin 14 is pushed into an annular groove 27 constituting a fourth stop means. The insert 25 has a coaxial female micrometer thread 28. In a prototype of the device this thread 28 has a pitch of 0,5 mm per revolution. On the upper end the insert 25 has a tubular, cylindrical collar 29.

Threaded into the thread 28 is a male thread 35 of a tubular knife holder 36 which is guided in a cylindrical boring 37 of the insert 25. In the embodiment of FIGS. 1–3 three lance shaped diamond knives 38 are mounted an the holder 36. In their upper part the knives 38 have a rectangular cross section and are glued into rectangular recesses 39 of the holder 36 which are parallel to the axis 2. On their lower end the knives 38 have facettes 40 forming two converging cutting edges 41 meeting in a knife tip 42. The tips 42 of all three knives 38 are on a common radius around the axis 2 and are adjusted such that they lay in a common radial plane perpendicular to the axis 2.

On the upper end a ring shaped head 46 is mounted on the holder 36 with set screws 47. The head 46 has a collar 48 surrounding the collar 29 of the insert 25. On a conical lower face 49 of the collar 48 a micrometer scale 50 is marked which cooperates with markings 51 on the collar 29 as is commonly known from micrometers. The angular position of the head 46 relative to the holder 36 is adjusted such that the accurate cutting depth, i.e. the destance with which the tips 42 extend beyond the contact surfaces 4 in the extended position of the insert 25, is accuratly readable. For avoiding backlash a proloaded spring 52 is mounted between the head 46 and the insert 25.

The insert 25 has a radial threaded boring 54 into which a locking screw 55 is screwed. When the desired cutting depth is adjusted by turning the head 46 relative to the insert 25 this adjustment is then fixed with the screw 55. In operation the thickness of the cornea of the patient's eye is measured and the cutting depth set to that thickness. The device is placed on the patient's eye and the suction pump switched on. Then the lever 10 is pushed in so that the insert 25 drops from its retracted position to the extended position shown in FIG. 1. The insert 25 with the holder 36 and the head 46 is turned by at least 120°. The suction pump is then switched off and the device removed. The rest of the operation is conventional.

In case the cornea is not completely cut through over the entire circumference the special scalpel 58 shown in FIGS. 5 through 8 is used to complete the cut. The scalpel 58 comprises a tubular handle 59 in which a shaft 60 is rotatably and slidably inserted. The shaft 60 has an actuating knob 61 on its rear end. A transverse pin 62 is mounted in the shaft 60. The pin 62 glides in a bayonet groove 63 of the handle 59. The groove 63 has a longitudinal section 64 and two axially spaced circumferential sections 65, 66. The rearward circumferential section 65 ends in axially extending recesses 67, 68 extending rearwardly and forwardly. The forward circumferential groove 66 ends in an axially rearwardly extending recess 69. The shaft 60 is preloaded into its retracted position by a spring (not shown) in which the pin 62 is situated in the section 65 or in the recess 67.

At the front end a small diamond knife 73 is mounted on the shaft 60. The knife 73 is prismatic and has two parallel side surfaces 74 and four facettes 75 forming two parallel opposed cutting edges 76 for cutting in both directions. A blunt metallic shoe 77 is mounted on the front end of the knife 73. The shoe 77 is basically frustro-pyramidal shaped and has rounded longer lateral lower edges 78 and short rounded edges 79 which extend somewhat beyond the cutting edges 76. The shoe 77 has a longitudinal rectangular groove 80 into which the front end of the knife 73 is braced or glued. In the retracted position of the shaft 60 the pin 62 rests in the recess 67 and the knife 73 is completely inside the handle 59. Because of the recess 68 the knife 73 cannot accidentally be moved into the extended postion by just pushing on the knob 61.

FIG. 4 shows a longitudinal section through the lower part of a second embodiment of the invention. The upper part of this embodiment is identical to the one of FIGS. 1 and 2. The embodiment of FIG. 4 mainly differs from the previously described one in that the knife 84 is a tubular ring shaped metal knife with a cylindrical outer surface 85 which is held in a cylindrical boring 86 of the knife holder 36 by a snap action fitting schematically represented by a leaf spring hook 86 snapped into a recess 88 of the knife 84. The leaf spring is attached to the holder 36 e.g. by spot welding. The rotary position of the knife 84 relative to the holder 36 is fixed by a transverse pin 89 mounted in the holder 36 and engaging in an axial slot 90 of the knife 84. The cutting edge 91 of the knife 84 is circular and coaxial with the axis 2. Its plane is perpendicular to that axis 2.

In this embodiment the device preferably comprises a set of knifes 84 of different diameters of the cutting edge 91, e.g. staggered in increments of 0.25 mm from e.g. 7 mm to 9 mm diameter. This ensures that only the damaged part of the cornea must be removed. The knife 84 is preferably of stainless steel and is intended for one-way use, i.e. it is discarded after the operation. This way a totally aseptic operation can be guaranteed. For dismounting the insert 25 is removed from the housing 1 by pushing the lever 10 and pulling the insert 25 with the holder 36 out. The hook 87 is released e.g. with a pin and the knife 84 pulled out.

The devices described above can also be used to cut a transplant out of a donor eye in the same way as described above. Before cutting, the inside pressure of the donor eye usually should be adjusted to a preselected level by methods known.

What we claim is:

1. A device for transplanting a cornea on a patient's eye, comprising:

a tubular housing having an axis and comprising a suction ring on a lower end face thereof with an annular recess communicating with a connector for connection to a suction pump, the housing having first stop means and second stop means;

a tubular insert mounted in the housing for rotation around the axis and axially displaceable, the insert having third stop means cooperating with the first stop means for defining an extended position of the insert and a fourth stop means coacting with the second stop means for defining a retracted position of the insert, the insert further having a micrometer female thread;

a tubular knife holder with a knife for cutting a circular cut into the cornea, the knife holder having a micrometer male thread threaded into the female thread and a head and the tubular knife holder being guided in said tubular insert;

a scale and a marking on the head and on the insert for preselecting a depth of the cut in the extended position of the tubular insert.

2. The device according to claim 1, wherein a rotary position of the knife holder relative to the insert is lockable by a locking means.

3. The device according to claim 1, wherein the knife comprises at least one lance shaped diamond knife.

4. The device according to claim 1, wherein the knife is a ring shaped metal knife with a circular cutting edge arranged in a plane perpendicular to the axis.

5. The device according to claim 4, wherein the knife is detachably mounted to the knife holder.

6. The device according to claim 5, further comprising a plurality of knives with different diameters of the cutting edge.

7. The device according to claim 4, wherein the second stop means is releasable for removing the insert from the housing.

8. The device according to claim 1, further comprising a scalpel comprising a handle, a shaft slidably inserted in the handle from a rest position into a cutting position, a diamond knife with at least one cutting edge mounted on a front end of the shaft, and a blunt shoe mounted on a front end of the knife, the knife extending beyond a front end of the handle in the cutting position and being inside that front end in the rest position.

* * * * *